United States Patent
Ono

(10) Patent No.: US 9,180,272 B2
(45) Date of Patent: Nov. 10, 2015

(54) INSTRUMENT FOR TREATING PATIENT WITH SEMICIRCULAR CANAL INJURY AND METHOD FOR PRODUCING SAME

(75) Inventor: Hidenori Ono, Setagaya-ku (JP)

(73) Assignee: ONO & CO., LTD, Tokyo (JP)

( * ) Notice: Subject to any disclaimer, the term of this patent is extended or adjusted under 35 U.S.C. 154(b) by 1010 days.

(21) Appl. No.: 13/319,671

(22) PCT Filed: May 13, 2010

(86) PCT No.: PCT/JP2010/058572
§ 371 (c)(1),
(2), (4) Date: Nov. 9, 2011

(87) PCT Pub. No.: WO2010/131779
PCT Pub. Date: Nov. 18, 2010

(65) Prior Publication Data
US 2012/0059362 A1    Mar. 8, 2012

(30) Foreign Application Priority Data
May 15, 2009 (JP) ................................. 2009-136688

(51) Int. Cl.
*A61M 21/00* (2006.01)
*G01C 9/18* (2006.01)
*A61B 5/11* (2006.01)

(52) U.S. Cl.
CPC ................. *A61M 21/00* (2013.01); *A61B 5/11* (2013.01); *G01C 9/18* (2013.01); *A61M 2021/0022* (2013.01); *A61M 2021/0044* (2013.01)

(58) Field of Classification Search
CPC ..................... A61M 21/00; A61M 2021/0022; A61M 2021/0044; A61B 5/11; A61B 5/1124; G01C 9/18

USPC ..................................... 33/301, 370, 377, 512
See application file for complete search history.

(56) References Cited

U.S. PATENT DOCUMENTS 3,871,104 A * 3/1975 Underhill, II .................. 33/262
5,966,680 A   10/1999 Butnaru
(Continued)

FOREIGN PATENT DOCUMENTS

JP    2009-022397 A    2/2009
WO   WO 2007/131325 A1   11/2007

OTHER PUBLICATIONS

Epley John M., The canalith repositioning procedure: For treatment of benign paroxysmal positional vertigo, Otolaryngology—Head and Neck Surgery, Sep. 1992, vol. 107, p. 399-404.

(Continued)

*Primary Examiner* — G. Bradley Bennett
(74) *Attorney, Agent, or Firm* — Holtz, Holtz, Goodman & Chick PC

(57) ABSTRACT

Disclosed is an instrument for treating a patient with semicircular canal injury, which is an instrument in the form of an exact enlarged model of human three semicircular canals having a structure wherein a liquid and a plurality of otolithic models, having a specific gravity larger than the specific gravity of said liquid, are enclosed within a hollow annular member made of a transparent resin and equipped with a screen at the position corresponding to the cupula in each of the three semicircular canals. Therein, said screen has such a mesh size as allowing the passage of said liquid but not allowing the passage of the otolithic models. Thus, an instrument for treating a patient with semicircular canal injury, whereby physical and mental pains can be alleviated in treating a patient with semicircular canal injury such as benign paroxysmal positional vertigo, is provided.

18 Claims, 2 Drawing Sheets

(56) References Cited

U.S. PATENT DOCUMENTS

| | | |
|---|---|---|
| 6,609,523 B1 | 8/2003 | Anthony |
| 2005/0223580 A1* | 10/2005 | Madsen .......................... 33/512 |
| 2007/0261702 A1 | 11/2007 | Bromwich |
| 2010/0010569 A1* | 1/2010 | Parker et al. .................... 607/57 |
| 2011/0152711 A1* | 6/2011 | Della Santina et al. ....... 600/546 |
| 2012/0059362 A1* | 3/2012 | Ono ................................. 606/1 |
| 2012/0316625 A1* | 12/2012 | Smith et al. ..................... 607/99 |
| 2014/0350640 A1* | 11/2014 | Patrick et al. ................... 607/57 |
| 2015/0068052 A1* | 3/2015 | Krueger .......................... 33/301 |

OTHER PUBLICATIONS

Extended European Search Report (EESR) dated Nov. 19, 2013 (in English) issued in counterpart European Application No. 10775029.1.

* cited by examiner

INSTRUMENT FOR TREATING PATIENT WITH SEMICIRCULAR CANAL INJURY AND METHOD FOR PRODUCING SAME

This application is the United States national phase application of International Application PCT/JP2010/058572 filed May 13, 2010.

TECHNICAL FIELD

The present invention relates to an instrument for treating a patient with semicircular canal injury and a method for producing the same. More specifically, the present invention relates to an instrument in the form of an enlarged model of three semicircular canals, which includes a liquid and otolithic models enclosed within a hollow annular member made of a transparent resin; an instrument for treating a patient with semicircular canal injury including the above instrument, which is to be attached to a headband member and used with the headband member being worn around the forehead of a patient; and a method for effectively producing the treatment instrument.

BACKGROUND ART

As semicircular canal injury, benign paroxysmal positional vertigo is known, for example. In this disease, when the head is quickly moved to change its direction up and down, from side to side, or the like, rotatory vertigo occurs, where the person feels if the head spins.

Incidentally, in the vestibule, which is the organ responsible for the sense of balance, there are three semicircular canals that play an important role in maintaining the balance of the body. The three semicircular canals include the following three semicircular canals, i.e., the anterior semicircular canal, the posterior semicircular canal, and the lateral semicircular canal. They have a structure in which they are at right angles to one another.

In the vestibule, further, there is an otolith organ. The structure of the otolith organ is such that the organ has a large number of dense short hairs, and minute stones (otoliths) are placed on the end portions thereof. The shaking of such otoliths allows the gravity and linear acceleration to be perceived.

When the head is moved, the lymph in the three semicircular canals also moves, and, together with this movement, hair cells create a nervous impulse to transmit the signal to the brain. The movement of the lymph in one semicircular canal corresponding to the direction in which the head moves becomes larger than the movement in the other two semicircular canals, and the brain thus recognizes the rotation of the head.

Thus, because of the functions of the vestibule and the three semicircular canals, the brain can recognize the rotation of the head and the linear movement, as well as acceleration of the body, whereby the brain performs the operation to maintain the balance of the body.

It sometimes happens that a large number of otoliths on the otolith organ in the vestibular organ are deviated from the original position for some reason, and float inside the semicircular canals or adhere to a region inside the semicircular canals called cupula (a narrow portion in each semicircular canal, which forms a narrow path for the movement of otoliths). When the head of a person is moved in this state, otoliths extraordinarily irritate the three semicircular canals, whereby the person feels giddy.

Like this, benign paroxysmal positional vertigo occurs due to the deviation of otoliths in the vestibule, followed by entry into the three semicircular canals, thereby irritating the three semicircular canals. Therefore, once the otoliths that have entered the semicircular canals are taken out in one way or another, vertigo can be eliminated completely.

As a method for removing otoliths that have entered the semicircular canals, physiotherapy is commonly used. In this method, the patient's head is moved back and forth and from side to side to apply acceleration to otoliths floating in the semicircular canals or otoliths adhering to the cupulae, thereby removing the otoliths from the semicircular canals (see, e.g., Nonpatent Document 1). However, this method is a trial-and-error method, and has a problem in that the treatment takes a long period of time and gives physical and mental pains to the patient.

PRIOR ART DOCUMENTS

Nonpatent Document

[Nonpatent Document 1] The canalithrepositioning procedure: For treatment of benign paroxysmal positional vertigo, Otolaryngol Head Neck Surg 107: 399-404, 1992.

SUMMARY OF THE INVENTION

Problems to be Solved by the Invention

Under such circumstances, an object of the present invention is to provide an instrument for treating a patient with semicircular canal injury, whereby physical and mental pains can be alleviated in treating a patient with semicircular canal injury such as benign paroxysmal positional vertigo; and a producing method for obtaining an exact enlarged model for the instrument.

Means for Solving the Problems

The present inventors conducted extensive research to achieve the above object. As a result, they found that when an instrument in the form of an exact enlarged model of human three semicircular canals having a specific structure made of a transparent resin is used as an instrument for treating a patient with semicircular canal injury, it is possible to alleviate physical and mental pains caused to the patient.

They also found that the instrument in the form of an exact enlarged model can be effectively produced by stereolithography using a photopolymerizable resin. The present invention was accomplished based on such findings.

That is, the prevent invention provides:

(1) an instrument for treating a patient with semicircular canal injury, which is an instrument in the form of an exact enlarged model of human three semicircular canals, and which has a structure in which a liquid and a plurality of otolithic models that have a specific gravity larger than the specific gravity of the liquid are enclosed within a hollow annular member made of a transparent resin and equipped with a screen at the position corresponding to the cupula in each of the three semicircular canals, the screen having such a mesh size as allowing the passage of the liquid but not allowing the passage of the otolithic models;

(2) an instrument for treating a patient with semicircular canal injury, which is an instrument in the form of an exact enlarged model of human three semicircular canals, and which has a structure in which a liquid and a plurality of otolithic models that have a specific gravity larger than the specific gravity of the liquid are enclosed within a hollow annular member made of a transparent resin and equipped with a screen at the position corresponding to the cupula in each of the three semicircular canals, the screen having such a mesh size as allowing the passage of the liquid but not allowing the passage of the otolithic models, and the instrument is attached to a headband member, and the headband member having the instrument attached thereto is worn around the forehead of a patient; and (3) the method for producing an instrument for treating a patient with semicircular canal injury according to (1) or (2) described above, which is a method for producing an instrument in the form of an exact enlarged model of human three semicircular canals, and wherein a molded body in the form of the three semicircular canals as enlarged is produced by stereolithography using a photopolymerizable resin that cures upon irradiation with a laser beam, the molded body including a hollow annular member made of a transparent resin and equipped with a screen at the position corresponding to the cupula in each of the three semicircular canals, a plurality of otolith models and a liquid are placed into the molded body through an opening in the molded body, and the opening is sealed.

Advantage of the Invention

According to the present invention, it is possible to provide an instrument for treating a patient with semicircular canal injury, whereby physical and mental pains can be reduced in quickly and reliably treating a patient with semicircular canal injury such as benign paroxysmal positional vertigo; and a producing method which can obtain an exact enlarged model for the instrument.

BEST MODES FOR CARRYING OUT THE INVENTION

First, the instrument for treating a patient with semicircular canal injury of the present invention will be explained.

The instrument for treating a patient with semicircular canal injury of the present invention has two aspects. An instrument for treating a patient with semicircular canal injury according to the first aspect (hereinafter sometimes simply referred to as treatment instrument I) is an instrument in the form of an exact enlarged model of human three semicircular canals, the instrument which has a structure in which a liquid and a plurality of otolithic models that have a specific gravity larger than the specific gravity of the liquid are enclosed within a hollow annular member made of a transparent resin and equipped with a screen at the position corresponding to the cupula in each of the three semicircular canals, the screen having such a mesh size as allowing the passage of the liquid but not allowing the passage of the otolithic models.

The screen for use in the present invention may be a wire screen, a screen made of natural or synthetic fibers, or a plastic screen. As a wire screen, stainless steel that is resistant to rust, for example, is preferable.

Figure 1:
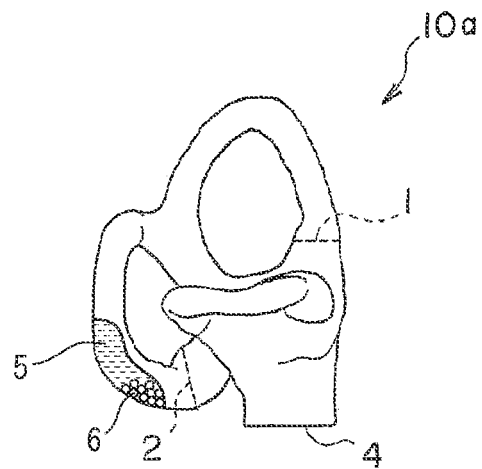
FIG. 1 shows an enlarged molded body in the form of three semicircular canals, which includes a hollow annular member made of a transparent resin, for producing an instrument in the form of an enlarged model of right three semicircular canals, as seen from the right side (earhole side)
Figure 2:
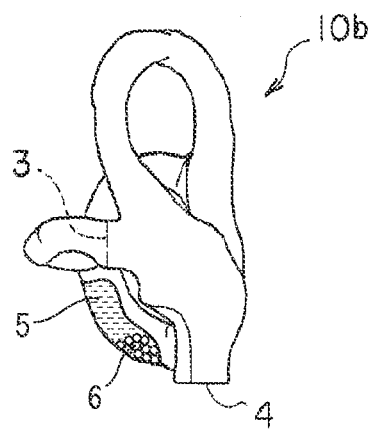
FIG. 2 shows an enlarged molded body in the form of three semicircular canals, which includes a hollow annular member made of a transparent resin, for producing an instrument in the form of an enlarged model of right three semicircular canals, as seen from the front.
Figure 3:
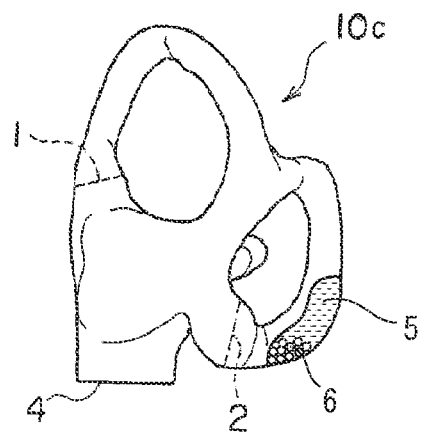
FIG. 3 shows an enlarged molded body in the form of three semicircular canals, which includes a hollow annular member made of a transparent resin, for producing an instrument in the form of an enlarged model of right three semicircular canals, as seen from the left side (brain side)

As shown in FIGS. 1 to 3, the instrument in the form of an exact enlarged model of human three semicircular canals in the present invention means that the shape thereof is just like the shape of the actual human three semicircular canals and is on a proportionally enlarged scale compared with the actual size. The joint and combination angles in the three semicircular canals are just like the real ones, and only the dimension is on an enlarged scale compared with the actual size. The instrument in the form of an exact enlarged model of three semicircular canals of the present invention does not include a mere geometric combination of three circular or elliptical rings.

Unless the shape is nearly identical to the real shape, the otolith movement in the model does not agree with the movement in the human body.

[Hollow Annular Member Made of Transparent Resin]

The hollow annular member made of a transparent resin used for the production of the treatment instrument I of the present invention is equipped with a screen at the position corresponding to the cupula in each of the three semicircular canals.

As such a hollow annular member, for example, in case of the production of an instrument in the form of an enlarged model of right three semicircular canals, the enlarged molded body including a hollow annular member made of a transparent resin shown in FIG. 1, FIG. 2, and FIG. 3 and represented by 10a, 10b, and 10c, respectively, can be mentioned.

The 10a shows the shape of an enlarged molded body in the form of right three semicircular canals, which includes the hollow annular member, as seen from the right side (earhole side), and 10b shows the shape of an enlarged molded body in the form of right three semicircular canals, which includes the hollow annular member, as seen from the front. Further 10c shows the shape of an enlarged molded body in the form of right three semicircular canals, which includes the hollow annular member, as seen from the left side (brain side).

In each figure, the reference numerals 1, 2, and 3 each represent a screen provided at the position corresponding to the cupula in each of the three semicircular canals. The screen is required to have such a mesh size as allowing the passage of the liquid mentioned below but not allowing the passage of the otolithic models. Materials therefor are not particularly limited, and it may be made of plastics or metals. However, in terms of durability, stainless steel is preferable. Further, the reference numeral 4 represents an opening in the enlarged molded body.

Incidentally, it is preferable that the enlarged molded body in the form of three semicircular canals is on a scale three to ten times the actual size of three semicircular canals. Further, in the case of left three semicircular canals, the shape that is symmetrical to the shape shown in FIG. 1 to FIG. 3 above is mentioned.

In the present invention, the enlarged molded body including the hollow annular member made of a transparent resin can be effectively formed by the below-mentioned producing method according to the present invention.

[Liquid and Otolithic Models]

As mentioned above, the treatment instrument I of the present invention has a structure in which a liquid and a plurality of otolithic models that have a specific gravity larger than the specific gravity of the liquid are enclosed within an enlarged molded body including a hollow annular member that is made of a transparent resin and equipped with a screen at the position corresponding to the cupula in each of the three semicircular canals.

The kind of the liquid is not particularly limited, but a liquid that is similar to the human lymph is preferable, and an edible oil or the like can be used, for example.

Meanwhile, with respect to the otolithic models, it is required that the specific gravity thereof is larger than the specific gravity of the liquid used. In particular, one having a specific gravity that is 1.1 to 1.5 times the specific gravity of the liquid is preferable. It is preferable that the particle diameter of the otolithic models is close to the particle diameter of the human otoliths. As such otolithic models, glass beads having a particle diameter of 0.5 to 5 mm can be used, for example.

Next, an instrument for treating a patient with semicircular canal injury according to the second aspect (hereinafter sometimes simply referred to as treatment instrument II) will be explained.

The treatment instrument II of the present invention is characterized in that the treatment instrument I mentioned above is attached to a headband member, and that the headband member having the treatment instrument I attached thereto is worn around the forehead of a patient.

Figure 4:
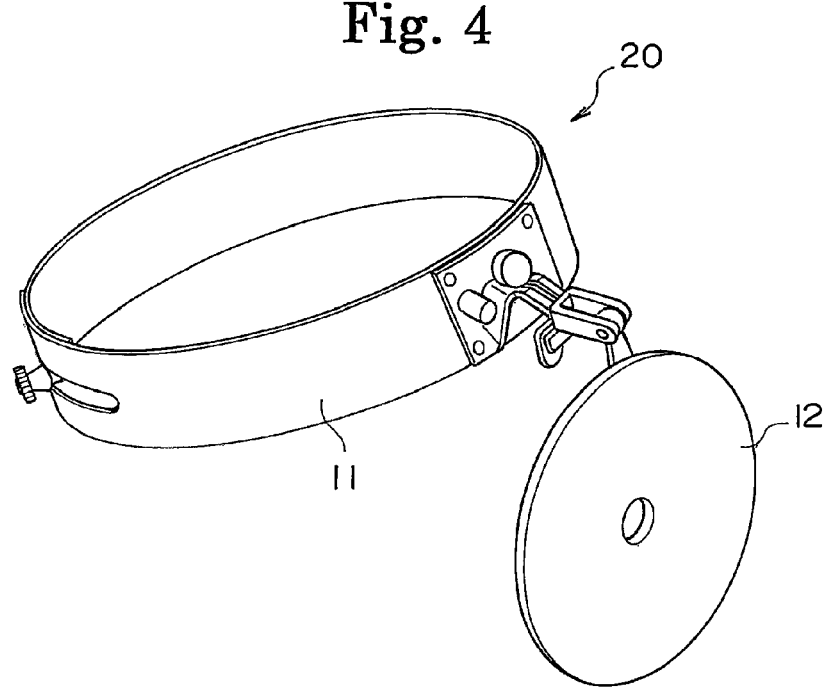
FIG. 4 is a perspective view of an example of a headband member for the attachment of an instrument for treating a patient with semicircular canal injury of the present invention.

An example of the headband member is the member shown in FIG. 4. FIG. 4 is a perspective view of an example of a headband member for the attachment of the treatment instrument I of the present invention. In FIG. 4, the reference numeral 20 represents a headband member, and 11 represents a belt-like portion for wearing around the forehead of a patient.

Figure 5:
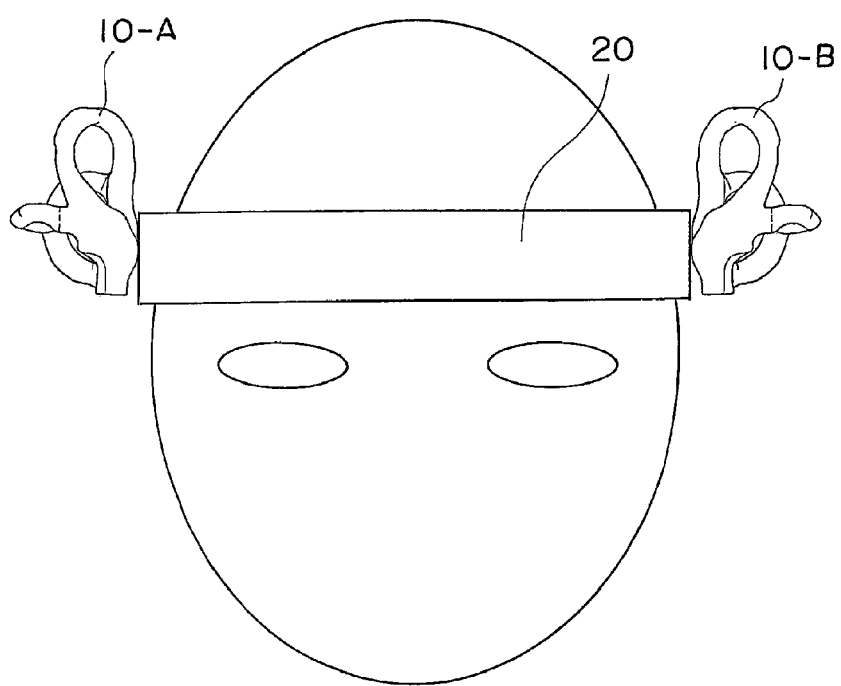
FIG. 5 is a front view of an example where an instrument for treating a patient with semicircular canal injury of the present invention attached to the headband member is worn around the forehead. In the figures, reference numerals 1, 2, and 3 represent a screen, 4 represents an opening, 5 represents a liquid, 6 represents otolithic models, 10a shows the shape of an enlarged molded body in the form of right three semicircular canals, which includes a hollow annular member, as seen from the right side (earhole side), 10b shows the shape of an enlarged molded body in the form of right three semicircular canals, which includes a hollow annular member, as seen from the front, 10c shows the shape of an enlarged molded body in the form of right three semicircular canals, which includes a hollow annular member, as seen from the left side (brain side), 10-A represents a treatment instrument I including an instrument in the form of an enlarged model of right three semicircular canals, 10-B represents a treatment instrument I including an instrument in the form of an enlarged model of left three semicircular canals, 11 represents a belt-like portion for wearing around the forehead of a patient, and 20 represents a headband member.

FIG. 5 is a front view of an example where the treatment instrument I of the present invention attached to the headband member is worn around the forehead. In FIG. 5, the reference numeral 10-A represents a treatment instrument I including an instrument in the form of an enlarged model of right three semicircular canals, and 10-B represents a treatment instrument I including an instrument in the form of an enlarged model of left three semicircular canals.

According to the present invention, a treatment instrument I including an instrument in the form of an enlarged model of three semicircular canals of the right or left side, which is the sick side having semicircular canal injury, is attached. However, if necessary, it is also possible to attach treatment instruments I including instruments in the form of enlarged models of both right and light three semicircular canals as shown in FIG. 5.

Next, the method for producing a treatment instrument I of the present invention will be explained.

[Method for Producing Treatment Instrument I]

The method for producing a treatment instrument I of the present invention is a method for producing an instrument in the form of an enlarged model of human three semicircular canals, and wherein a molded body in the form of the three semicircular canals as enlarged is produced by stereolithography using a photopolymerizable resin that cures upon irradiation with a laser beam, the saped body including a hollow annular member made of a transparent resin and equipped with a screen at the position corresponding to the cupula in each of the three semicircular canals, a plurality of otolith models and a liquid are placed into the molded body through an opening in the molded body; and the opening is sealed.

In the method for producing a treatment instrument I of the present invention, first, using a photopolymerizable resin that cures upon irradiation with a laser beam, a molded body in the form of enlarged three semicircular canals, which includes a hollow annular member made of a transparent resin and equipped with a screen at the position corresponding to the cupula in each of the three semicircular canals, is formed by stereolithography.

In the present invention, stereolithography is employed, which is excellent in terms of molding rate, the transparency of the resulting molded body, and accuracy. Therefore, as the photopolymerizable resin, those curable upon irradiation with a UV laser beam are used. As such photopolymerizable resins, for example, epoxy-acrylate-based, ester-acrylate-based, urethane-acrylate-based, and polyol-acrylate-based oligomers are usable.

In the stereolithography, specifically, a series of slice data with as fine pitches as possible (not more than 1 mm, preferably about 0.3 mm), which are obtained by photographing test subjects for the production of an enlarged model of three semicircular canals, are written in CD-R as DICOM data (abbreviation of Digital Imaging and Communication in Medicine: a standard developed by the American College of Radiology (ACR) and the National Electrical Manufacturers Association (NEMA), defining the format of medical images taken by CT, MRI, or the like and the communication protocol between medical imagers for such images), then they are read by "Mimics, software for the 3D conversion and editing of slice data", and calculation parameters for correction and 3D conversion, etc., are adjusted so that the region for modeling (area of interest) will be in satisfactory form.

In the present invention, the target area is the semicircular canals, an area that forms a hollow tube structure in a human bone. Accordingly, the extraction threshold (Hounsfield value) is set at a low value that is inapplicable to either bone or soft tissues (here, the extraction lower limit is −1024 set as air, and, while slowly increasing the upper limit, the basic extraction region is set at a value of 225, which is the most desirable as the shape of semicircular canals). Further, partial corrections are made so that the shape of target area on the data has a desirable hollow tube structure, thereby achieving 3D conversion.

As such a molded body in the form of enlarged three semicircular canals formed by stereolithography, which includes a hollow annular member equipped with the screen, the molded body having the shape shown in FIG. 1 to FIG. 3 above can be mentioned, for example.

In the present invention, the plurality of otolithic models and the liquid are placed inside through the opening (e.g., reference numeral 4 in FIG. 1 to FIG. 3) in the molded body, and the opening is sealed in such a manner that the entrance of air can be minimized; as a result, the treatment instrument I of the present invention can be obtained. The method for sealing is not particularly limited, and a method in which sealing is achieved with a rubber plug, which is used in a chemical experiment or the like, can be employed, for example.

EXAMPLES

Next, the present invention will be explained in further detail with reference to the examples, but the present invention is not limited to these examples.

Example 1

High-resolution tomographic image data of the human right and/or left cranial bone site [DICOM (as above) data output from CT photographed in a 0.3 mm pitch] was read into a slice-image editing software [manufactured by Materialise, "Mimics"]. On the software, using the threshold corresponding to the internal cavity shape of three semicircular canals (Hounsfield values from −1024 to 225), internal three-dimensional shape data of the three semicircular canals were prepared, and film thickness was added to the surface shape of the internal three-dimensional shape of the three semicircular canals to give three-dimensional shape data of the hollow annular structure of the three semicircular canals. Thus, three-dimensional data were prepared, where the three-dimensional shape data of the hollow annular structure of the three semicircular canals are floating in the air.

Next, the three-dimensional data were enlarged five times the original size and input into the computer in a precise laminating machine [manufactured by CMET Inc., diode-pumped solid-state laser "SOLIFORM-600"] equipped with a head that allows a photopolymerizable resin in the form of a laminate of 0.2-mm-thick thin layers to cure upon irradiation with a laser beam having a spot diameter of 0.25 mm. Next, based on the three-dimensional data input into the computer, the data of the three semicircular canals' wall portion area, which were obtained from the level surface parallel to the bottom of the three-dimensional data by cutting the three-dimensional data in round slices for every 0.2-mm-thick thin-film unit, were output, and the photopolymerizable resin was irradiated with a laser beam (liquid-surface input value: 200 mW, 60 k Hz) to form the three-semicircular-canal portion having a thin-film unit thickness, whereby an operation to form a three semicircular canals' wall was performed. This operation was sequentially repeated for every thin-layer unit from the lower end to upper end of the three-dimensional data to give a massive matrix of the photopolymerizable resin in the three-dimensional, three semicircular canals' wall shape corresponding to the three-dimensional data.

Next, from the massive matrix, uncured resin present inside was taken out through the opening in the molded body in the form of three semicircular canals, thereby forming a molded body on a scale equivalent to about five times the actual-size three semicircular canals as shown in FIG. 1 to FIG. 3, which includes the hollow annular structure made of a transparent resin.

Incidentally, as the photopolymerizable resin, an epoxy-based photopolymerizable resin [trade name "TSR-829", manufactured by CMET Inc., curable with a laser beam from a laser diode, 25° C. viscosity: 205 mPa-s, 25° C. specific gravity: 1.08] was used. When the photopolymerizable resin is cured with a laser beam, the cured resin physical properties are as follows: tensile strength: 46 MPa, tensile elongation: 7 to 10%, tensile modulus: 1750 MPa, flexural strength: 68 MPa, flexural modulus: 2070 MPa, impact strength: 34 J/m, high-load HDT: 49 to 50° C., low-load HDT: 54° C., glass transition temperature: 66° C., surface hardening (Shore D): 83, shrinkage: 5.1%, appearance: transparent.

Further, at the position corresponding to each cupula in three semicircular canals (a narrow portion in each semicircular canal, which forms a narrow path for the movement of otoliths), for example, in the case of the right side, as indicated by reference numerals 1, 2, and 3 in FIG. 1 to FIG. 3, a screen made of a photopolymerizable resin (whose mesh size allows the passage of the edible oil mentioned below but does not allow the passage of the otolithic models (glass beads)) was provided.

Next, through the opening in the thus-formed hollow annular molded body, otolithic models (glass beads having a particle diameter of 0.5 to 5 mm) were suitably placed inside, and, at the same time, an edible oil, which was selected to suit the speed of the movement of otoliths within three semicircular canals and also in consideration of the location of use, was placed inside. After that, the opening was sealed with a rubber plug for chemical experiments, whereby a model of right and/or left three semicircular canals made of a transparent resin was produced.

In the case where the thus-obtained three-semicircular-canal model made of a transparent resin is used as an instrument for treating semicircular canal injury, for example, the three-semicircular-canal model is attached to the headband member 20 shown in FIG. 4, and the belt-like portion 11 of the headband member is worn around the forehead of a patient with semicircular canal injury, as shown in FIG. 5. Then, while visually observing the movement of the otolithic models (glass beads) enclosed within the three-semicircular-canal model from the outside, the patient's head is moved so that otolithic models move to the predetermined position. The treatment is thus performed.

INDUSTRIAL APPLICABILITY

The instrument for treating a patient with semicircular canal injury of the present invention makes it possible to alleviate physical and mental pains in treating a patient with semicircular canal injury such as benign paroxysmal positional vertigo.

Further, according to the method for producing a treatment instrument of the present invention, a highly transparent and reliable treatment instrument can be produced at a high molding rate.

The invention claimed is:

1. An instrument for treating a patient with semicircular canal injury, which is an instrument in the form of an exact enlarged model of human three semicircular canals and which has a structure in which a liquid and a plurality of otolithic models that have a specific gravity larger than the specific gravity of said liquid are enclosed within a hollow annular member made of a transparent resin and equipped with a screen at the position corresponding to the cupula in each of the three semicircular canals, the screen having such a mesh size as allowing the passage of said liquid but not allowing the passage of the otolithic models.

2. An instrument for treating a patient with semicircular canal injury, which is an instrument in the form of an exact enlarged model of human three semicircular canals and which has a structure in which a liquid and a plurality of otolithic models that have a specific gravity larger than the specific gravity of said liquid are enclosed within a hollow annular member made of a transparent resin and equipped with a screen at the position corresponding to the cupula in each of the three semicircular canals, the screen having such a mesh size as allowing the passage of said liquid but not allowing the passage of the otolithic models; and the instrument is attached to a headband member, and the headband member having the instrument attached thereto is worn around the forehead of a patient.

3. A method for producing an instrument for treating a patient with semicircular canal injury according to claim 1, which is a method for producing an instrument in the form of an exact enlarged model of human three semicircular canals, and wherein a molded body in the form of the three semicircular canals as enlarged is produced by stereolithography using a photopolymerizable resin that cures upon irradiation with a laser beam, the molded body including a hollow annular member made of a transparent resin and equipped with a screen at the position corresponding to the cupula in each of the three semicircular canals; a plurality of otolith models and a liquid are placed into the molded body through an opening in the molded body; and the opening is sealed.

4. A method for producing an instrument for treating a patient with semicircular canal injury according to claim 2, which is a method for producing an instrument in the form of an exact enlarged model of human three semicircular canals, and wherein a molded body in the form of the three semicircular canals as enlarged is produced by stereolithography using a photopolymerizable resin that cures upon irradiation with a laser beam, the molded body including a hollow annular member made of a transparent resin and equipped with a screen at the position corresponding to the cupula in each of the three semicircular canals; a plurality of otolith models and a liquid are placed into the molded body through an opening in the molded body; and the opening is sealed.

5. The instrument for treating a patient with semicircular canal injury according to claim 1, wherein the transparent resin is a cured product of a photopolymerizable resin that cures upon irradiation with a laser beam.

6. The instrument for treating a patient with semicircular canal injury according to claim 5, wherein the photopolymerizable resin that cures upon irradiation with a laser beam is an epoxy-based photopolymerizable resin.

7. The instrument for treating a patient with semicircular canal injury according to claim 5, wherein the photopolymerizable resin that cures upon irradiation with a laser beam is a photopolymerizable resin curable upon irradiation with a UV laser beam.

8. The instrument for treating a patient with semicircular canal injury according to claim 7, wherein the photopolymerizable resin curable upon irradiation with a UV laser beam is selected from the group consisting of an epoxy-acrylate-based oligomer, an ester-acrylate-based oligomer, an urethane-acrylate-based oligomer, and a polyol-acrylate-based oligomer.

9. The instrument for treating a patient with semicircular canal injury according to claim 2, wherein the transparent resin is a cured product of a photopolymerizable resin that cures upon irradiation with a laser beam.

10. The instrument for treating a patient with semicircular canal injury according to claim 9, wherein the photopolymerizable resin that cures upon irradiation with a laser beam is an epoxy-based photopolymerizable resin.

11. The instrument for treating a patient with semicircular canal injury according to claim 9, wherein the photopolymerizable resin that cures upon irradiation with a laser beam is a photopolymerizable resin curable upon irradiation with a UV laser beam.

12. The instrument for treating a patient with semicircular canal injury according to claim 11, wherein the photopolymerizable resin curable upon irradiation with a UV laser beam is selected from the group consisting of an epoxy-acrylate-based oligomer, an ester-acrylate-based oligomer, an urethane-acrylate-based oligomer, and a polyol-acrylate-based oligomer.

13. The method for producing an instrument for treating a patient with semicircular canal injury according to claim 3, wherein the photopolymerizable resin that cures upon irradiation with a laser beam is an epoxy-based photopolymerizable resin.

14. The method for producing an instrument for treating a patient with semicircular canal injury according to claim 4, wherein the photopolymerizable resin that cures upon irradiation with a laser beam is an epoxy-based photopolymerizable resin.

15. The method for producing an instrument for treating a patient with semicircular canal injury according to claim 3, wherein the photopolymerizable resin that cures upon irradiation with a laser beam is a photopolymerizable resin curable upon irradiation with a UV laser beam.

16. The method for producing an instrument for treating a patient with semicircular canal injury according to claim 15, wherein the photopolymerizable resin curable upon irradiation with a UV laser beam is selected from the group consisting of an epoxy-acrylate-based oligomer, an ester-acrylate-based oligomer, an urethane-acrylate-based oligomer, and a polyol-acrylate-based oligomer.

17. The method for producing an instrument for treating a patient with semicircular canal injury according to claim 4, wherein the photopolymerizable resin that cures upon irradiation with a laser beam is a photopolymerizable resin curable upon irradiation with a UV laser beam.

18. The method for producing an instrument for treating a patient with semicircular canal injury according to claim 17, wherein the photopolymerizable resin curable upon irradiation with a UV laser beam is selected from the group consisting of an epoxy-acrylate-based oligomer, an ester-acrylate-based oligomer, an urethane-acrylate-based oligomer, and a polyol-acrylate-based oligomer.

* * * * *